(12) United States Patent
Shimoda et al.

(10) Patent No.: US 10,837,002 B2
(45) Date of Patent: Nov. 17, 2020

(54) ARTIFICIAL PERITONEAL TISSUE AND METHOD FOR PRODUCING SAME

(71) Applicants: HIROSAKI UNIVERSITY, Hirosaki (JP); OSAKA UNIVERSITY, Suita (JP)

(72) Inventors: Hiroshi Shimoda, Hirosaki (JP); Yoshiya Asano, Hirosaki (JP); Mitsuru Akashi, Suita (JP); Michiya Matsusaki, Toyonaka (JP)

(73) Assignees: HIROSAKI UNIVERSITY, Hirosaki (JP); OSAKA UNIVERSITY, Suita (JP)

( * ) Notice: Subject to any disclaimer, the term of this patent is extended or adjusted under 35 U.S.C. 154(b) by 46 days.

(21) Appl. No.: 15/507,083

(22) PCT Filed: Aug. 25, 2015

(86) PCT No.: PCT/JP2015/073888
§ 371 (c)(1),
(2) Date: Feb. 27, 2017

(87) PCT Pub. No.: WO2016/031824
PCT Pub. Date: Mar. 3, 2016

(65) Prior Publication Data
US 2017/0283778 A1    Oct. 5, 2017

(30) Foreign Application Priority Data
Aug. 28, 2014 (JP) ................. 2014-173502

(51) Int. Cl.
C12N 5/071       (2010.01)
C12N 11/02       (2006.01)

(52) U.S. Cl.
CPC ............ *C12N 5/0697* (2013.01); *C12N 11/02* (2013.01); *C12N 2502/1192* (2013.01); *C12N 2502/1323* (2013.01); *C12N 2502/28* (2013.01); *C12N 2513/00* (2013.01); *C12N 2533/52* (2013.01); *C12N 2533/54* (2013.01); *C12N 2533/90* (2013.01)

(58) Field of Classification Search
CPC .......... C12N 5/0697; C12N 11/02; C12N 2502/1192; C12N 2502/1323; C12N 2502/28; C12N 2513/00; C12N 2533/52; C12N 2533/54; C12N 2533/90
See application file for complete search history.

(56) References Cited

U.S. PATENT DOCUMENTS

2007/0207540 A1   9/2007  Akashi et al.
2016/0058917 A1   3/2016  Miyajima et al.

FOREIGN PATENT DOCUMENTS

| JP | 2005-608 A | 1/2005 |
| JP | 2007-77026 A | 3/2007 |
| JP | 2007-228921 A | 9/2007 |
| JP | 2012-115254 A | 6/2012 |
| JP | WO 2014/115776 A1 | 7/2014 |

OTHER PUBLICATIONS

Baldwin et al. In vitro pre-vascularisation of tissue-engineered constructs A co-culture perspective. Vascular Cell 2014, 6:13 (p. 1-16) (Year: 2014).*
Sukmana. Microvascular Guidance: A Challenge to Support the Development of Vascularised Tissue Engineering Construct. The Scientific World Journal Volume 2012, Article ID 201352, 10 pages (Year: 2012).*
Yung et al. Pathophysiological Changes to the PeritonealMembrane during PD-Related Peritonitis: The Role ofMesothelial Cells. Mediators of Inflammation. vol. 2012, Article ID 484167, 21 pages (Year: 2012).*
Yoshida et al. Multilayered Blood Capillary Analogs in Biodegradable Hydrogels for In Vitro Drug Permeability Assays. Adv. Funct. Mater. 2013, 23, 1736-1742 (Year: 2013).*
International Search Report dated Dec. 1, 2015 in PCT/JP2015/073888.
International Preliminary Report on Patentability dated Mar. 2, 2017 in PCT/JP2015/073888.
H. Kuga, et al., "Construction of a Transplantable Tissue-Engineered Artificial Peritoneum" European Surgical Research, vol. 36, 2004, pp. 323-330.
Margot N. Schilte, et al., "Factors Contributing to Peritoneal Tissue Remodeling in Peritoneal Dialysis" Peritoneal Dialysis International, vol. 29, 2009, pp. 605-617.
Marcin P. Iwanicki, et al., "Ovarian Cancer Spheroids Use Myosin-Generated Force to Clear the Mesothelium" Cancer Discovery, vol. 1, No. 2, 2011, 16 pages.
Nicola Di Paolo, et al., "Atlas of Peritoneal Histology in Normal Conditions and During Peritoneal Dialysis" Peritoneal Dialysis International, vol. 20, No. 3, 2000, 99 pages.
Akihiro Nishiguchi, et al., "Effects of Angiogenic Factors and 3D-microenvironments on Vascularization within Sandwich Cultures" Biomaterials, vol. 35, No. 17, 2014, pp. 4739-4748.
Yoshiya Asano, et al., "Ultrastructure of blood and lymphatic vascular networks in three-dimensional cultured tissues fabricated by extracellular matrix nanofilm-based cell accumulation technique" Microscopy, vol. 63, No. 3, 2014, pp. 219-226 and cover pages.
David G. Jayne, et al., "A three-dimensional in-vitro model for the study of peritoneal tumour metastasis" Clinical and Experimental Metastasis, vol. 17, No. 6, 1999, pp. 515-523.
Extended European Search Report dated Jan. 23, 2018 in the corresponding European Patent Application No. 15835587.5 (7 pages).

(Continued)

*Primary Examiner* — Taeyoon Kim
(74) *Attorney, Agent, or Firm* — Oblon, McClelland, Maier & Neustadt, L.L.P.

(57) ABSTRACT

The present disclosure relates to: an artificial peritoneal tissue comprising a cellular tissue and a mesothelial cell layer that covers the surface of the cellular tissue, wherein the cellular tissue comprises a fibroblast, an extracellular matrix, and a vascular endothelial cell and/or a lymphatic endothelial cell each capable of forming a lumen; and a method for producing the artificial peritoneal tissue.

3 Claims, 1 Drawing Sheet

(56) References Cited

OTHER PUBLICATIONS

Hilary A. Kenny, et al., "Use of a novel 3D culture model to elucidate the role of mesothelial cells, fibroblasts and extra-cellular matrices on adhesion and invasion of ovarian cancer cells to the omentum", International Journal of Cancer, vol. 121. No. 7, XP008162178, Oct. 1, 2007, pp. 1463-1472.

Akihiro Nishiguchi et al., "Rapid Construction of Three-Dimensional Multilayered Tissues with Endothelial Tube Networks by the Cell-Accumulation Technique", Advanced Materials, vol. 23, No. 31. XP-002753112, Aug. 16, 2011, pp. 3506-3510.

Asano et al, "Construction of artificial human peritoneal tissue by cell-accumulation technique and its application for visualizing morphological dynamics of cancer peritoneal metastasis", *Biochemical and Biophysical Research Communications*, vol. 494, (2017) pp. 213-219.

Asano et al, "Construction of artificial human peritoneal tissue by cell-accumulation technique and its application for visualizing morphological dynamics of caner peritoneal metastasis", *Biochemical and Biophysical Research Communications*, (2017) vol. 494, pp. 213-219.

Asano et al, "Construction of artificial human peritoneal tissue by cell-accumulation technique and its application for visualizing morphological dynamics of cancer peritoneal metastasis", *Biochemical and Biophysical Research Communications*, 2017, vol. 494, pp. 213-219.

Asano et al, "Transplantation of three-dimensional artificial human vascular tissues fabricated using an extracellular matrix nanofilm-based cell-accumulation technique", *J. Tissue Eng. Regen. Med.*, 2015, pp. 1-5 DOI: 10.1002/term.2018.

Asano et al, "Transplantation of artificial human lymphatic vascular tissues fabricated using a cell-accumulation technique and their engraftment in mouse tissue with vascular remodeling", *J. Tissue Eng. Regen. Med.*, 2017, pp. 1-10 DOI: 10.1002/term.2570.

* cited by examiner

[Fig. 1]
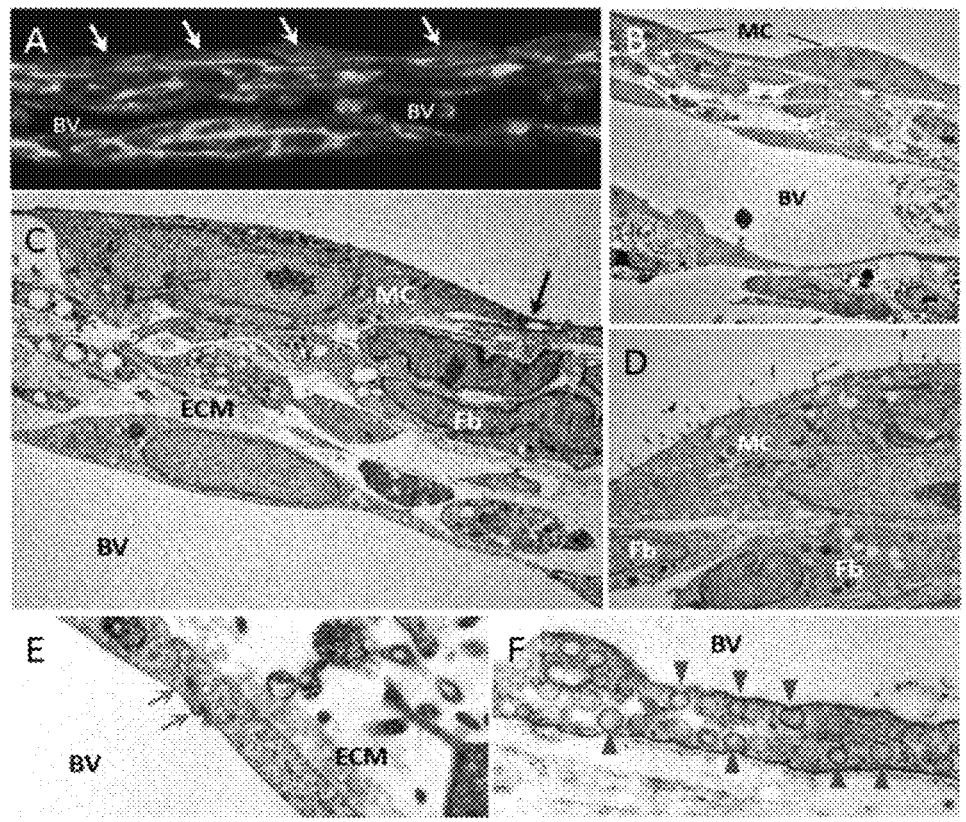
[Fig. 2]
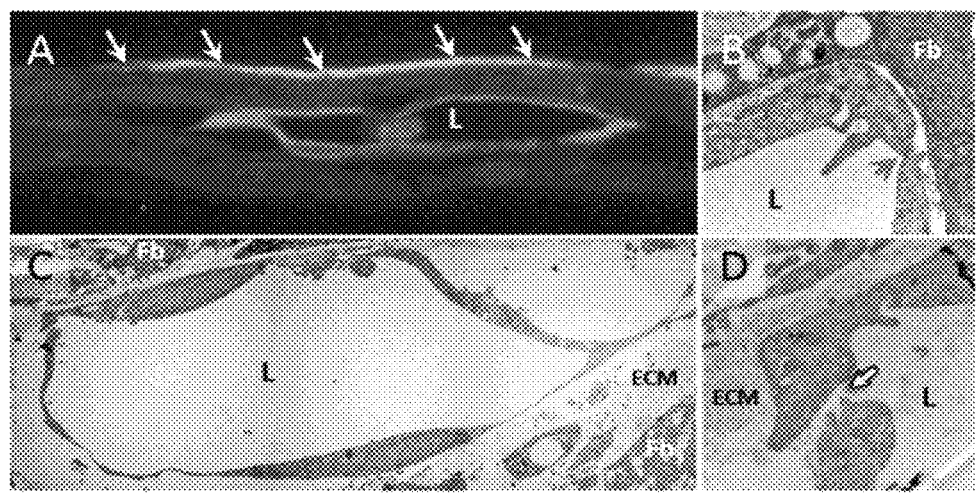

ARTIFICIAL PERITONEAL TISSUE AND METHOD FOR PRODUCING SAME

TECHNICAL FIELD

The present disclosure relates to an artificial peritoneal tissue and a method for producing the same.

BACKGROUND ART

In recent years, for the purpose of application of genetic engineering, molecular biology, and cell engineering to the field of medical care, there has been a demand for development of biomaterials such as artificial organs and implant materials by tissue engineering, and in vitro tissue engineering has been drawing attention of researchers (for example, Patent Documents 1 and 2). To construct a three-dimensional tissue, the following is necessary: cultured cells to serve as a construction component; a scaffold such as artificial material, or extracellular matrix (ECM); and a stimulus to induce histogenesis. To date, various tissue models have been reported.

The peritoneum is a continuous biological membrane covering from the abdominal wall and all the intraabdominal organs to some pelvic organs, and is constituted of a mesothelial cell monolayer and connective tissue that contains a vascular network, a lymphatic network, and the like. It has been traditionally known that the peritoneum is intimately involved in metastasis of cancer. It is known that many types of cancers of pelvic organs, such as the digestive tract and the ovary, are exfoliated into the abdominal cavity and then attached to the peritoneum for invasion (peritoneal metastasis), leading to further metastasis spreading through blood vessels and lymphatic vessels. On the other hand, peritoneal dialysis using the peritoneum is performed as one of dialysis therapies. However, long-term peritoneal dialysis reportedly causes hypofunction, hardening, and/or thickening of the peritoneum to eventually lead to encapsulating peritoneal sclerosis (EPS), or the like.

PRIOR ART DOCUMENTS

Patent Documents

Patent Document 1: Japanese Patent Application Publication No. 2007-228921
Patent Document 2: Japanese Patent Application Publication No. 2012-115254

DISCLOSURE OF THE INVENTION

Problems to be Solved by the Invention

Under the above-described circumstances, researches have been conducted to investigate the mechanisms of generating peritoneal metastasis, encapsulating peritoneal sclerosis, and the like, and to prevent and treat these diseases. In these researches, laboratory animals such as mice are currently used. In consideration of clinical application to humans, and the like, however, researches using peritoneal tissue that is more similar to peritoneal tissue in a human living body are needed. Therefore, there has been a demand for development of an artificial peritoneal tissue that can reproduce an environment more similar to the environment of peritoneal tissue in a human living body.

Means for Solving the Problems

The present inventors have intensively studied and, as a result, have successfully completed an artificial peritoneal tissue comprising a cellular tissue and a mesothelial cell layer that covers a surface of the cellular tissue, the cellular tissue comprising a fibroblast, an extracellular matrix, and at least one of a vascular endothelial cell and a lymphatic endothelial cell forming a lumen.

Effects of the Invention

The present disclosure provides an artificial peritoneal tissue that can reproduce an environment more similar to the environment of peritoneal tissue in a human living body, and a method for producing the same.

BRIEF DESCRIPTION OF THE DRAWINGS

FIG. 1 shows images of an artificial peritoneal tissue of Example 1, as an example. FIG. 1A is an optical microscope image, and each of FIGS. 1B to 1F is a transmission electron microscope image.

FIG. 2 shows images of an artificial peritoneal tissue of Example 2, as an example. FIG. 2A is an optical microscope image, and each of FIG. 2B to 2D is a transmission electron microscope image.

MODE FOR CARRYING OUT THE INVENTION

In one aspect, the present disclosure relates to an artificial peritoneal tissue comprising a cellular tissue and a mesothelial cell layer that covers a surface of the cellular tissue, the cellular tissue comprising fibroblast, an extracellular matrix, and at least one of a vascular endothelial cell and a lymphatic endothelial cell forming a lumen.

In other aspect, the present disclosure relates to a method for producing an artificial peritoneal tissue comprising a cellular tissue and a mesothelial cell layer that covers a surface of the cellular tissue, the cellular tissue comprising a fibroblast, an extracellular matrix, and at least one of a vascular endothelial cell and a lymphatic endothelial cell forming a lumen, the method comprising:
culturing at least one of a vascular endothelial cell and a lymphatic endothelial cell, a fibroblast, and an extracellular matrix to form the cellular tissue; and
placing a mesothelial cell on the cellular tissue.

The term "artificial peritoneal tissue" used in the present disclosure refers to a cell population that can function as peritoneal tissue and can be used as a functional or structural model of the peritoneum. Examples of the artificial peritoneal tissue of the present disclosure can include a tissue that has a structure resembling that of the peritoneum in a living organism; a model capable of reproducing a peritoneal function of a living organism; and a model for use to reproduce the function.

[Artificial Peritoneal Tissue]

In one aspect, the present disclosure relates to an artificial peritoneal tissue comprising a cellular tissue and a mesothelial cell layer that covers a surface of the cellular tissue, the cellular tissue comprising a fibroblast, an extracellular matrix, and at least one of a vascular endothelial cell and a lymphatic endothelial cell forming a lumen (hereinafter, also called "the artificial peritoneal tissue of the present disclosure").

The artificial peritoneal tissue of the present disclosure comprises a cellular tissue and a mesothelial cell. In one embodiment, the artificial peritoneal tissue of the present disclosure has the following configuration where: a mesothelial cell layer forms a covering structure; and the mesothelial cell layer is bound via an extracellular matrix to a tissue constituted of a fibroblast and at least one of a capillary vessel-like structure and a lymphatic-vessel-like structure. Namely, in one embodiment, the artificial peritoneal tissue of the present disclosure comprises an extracellular matrix between a fibroblast and a mesothelial cell. The artificial peritoneal tissue of the present disclosure can reproduce a peritoneal tissue structure, preferably a peritoneal tissue function, more similar to those in a living organism.

<Cellular Tissue>

In one embodiment, the cellular tissue is a cell assembly containing a fibroblast, an extracellular matrix, and at least one of a vascular endothelial cell and a lymphatic endothelial cell, and has a lumen therein containing at least one of a vascular endothelial cell and a lymphatic endothelial cell. In other embodiment, the cellular tissue has a structure in which cell layers each constituted of a fibroblast and an interstitial tissue sandwiches a vessel network constituted of at least one of a vascular endothelial cell and a lymphatic endothelial cell.

The term "lumen" used in the present disclosure refers to a hollow and tubular structure formed by cells including at least one of a vascular endothelial cell and a lymphatic endothelial cell. Cells that constitute a wall of the lumen include either a vascular endothelial cell or a lymphatic endothelial cell. In one embodiment, it is preferable that the cells that constitute the wall of the lumen are formed by substantially of either vascular endothelial cells or lymphatic endothelial cells. Examples of the structure of the lumen include a capillary vessel-like structure and a lymphatic-vessel-like structure. In one embodiment, the lumen forms a vessel network within the cellular tissue. In other embodiment, the lumen may form a mesh-like network such as a capillary vessel network or a lymphatic network.

The lumen formed by vascular endothelial cells is formed so that its structure is more similar to the structure of a capillary vessel in a living organism. From this viewpoint, in one embodiment, adjacent vascular endothelial cells preferably form cell-cell adhesion. An inner wall of the lumen is formed so that its structure is more similar to the structure of a capillary vessel in a living organism. From this viewpoint, in other embodiment, it is preferable that the inner wall of the lumen is rich in vesicle-like structure.

The lumen formed by vascular endothelial cells has, but is not limited to, a diameter ranging from, for example, 5 μm to 28 μm. In one embodiment, the artificial peritoneal tissue of the present disclosure preferably has such effects that an ingredient of a medium can easily reach a cell within the cellular tissue and the structure of the tissue is likely to be retained. The artificial peritoneal tissue of the present disclosure can also benefit researches on a peritoneum and evaluation of a peritoneum by making it easier to visualize the process of invasion of cancer cells and the like into a blood-vessel-like structure and also by making it easier to visualize the movement of cancer cells and the like in a blood-vessel-like structure. The diameter of the lumen can be measured by a conventionally known method, such as a method using an immunostaining image of vascular endothelial cells.

The lumen formed by lymphatic endothelial cells is formed so that its structure is more similar to the structure of a lymphatic capillary in a living organism. From this viewpoint, in one embodiment, the lumen preferably has an area where adjacent lymphatic endothelial cells form cell-cell adhesion and an area where adjacent lymphatic endothelial cells are away from each other.

In one embodiment, the fibroblasts in the cellular tissue are arranged via an extracellular matrix and form a three-dimensional structure.

The concentration of the fibroblasts in the cellular tissue ranges from, for example, $4 \times 10^8$ cells/cm$^3$ to $1.2 \times 10^9$ cells/cm$^3$, preferably from $1.0 \times 10^9$ cells/cm$^3$ to $1.2 \times 10^9$ cells/cm$^3$, for the reasons of creating an optimum microenvironment for lumen formation.

In one embodiment, each of the fibroblast, the endothelial cell, and the lymphatic endothelial cell may be derived from either a human or a non-human animal. In other embodiment, each of these cells may be a cell derived from a mesenchymal stem cell, from an embryonic stem cell, from an induced pluripotent stem cell, or the like. In another embodiment, each of these cells may be a cultured cell. Examples of the cultured cell include, but are not limited to, a primary cultured cell, a passaged cell, and a cell derived from a cell line.

In one embodiment, the cellular tissue may further comprise other cells different from the above-mentioned cells. Examples of the other cells different from the above-mentioned cells include, but are not limited to, a pericyte and a smooth muscle cell. The other cells may be derived from either a human or a non-human animal. In other embodiment, each of the other cells may be a cell derived from a mesenchymal stem cell, from an embryonic stem cell, from an induced pluripotent stem cell, or the like. In another embodiment, each of the other cells may be a cultured cell. Examples of the cultured cell include, but are not limited to, a primary cultured cell, a passaged cell, and a cell derived from a cell line.

In one embodiment, the extracellular matrix may contain a substance capable of playing the above-described roles in cell culturing in vitro, an artificially synthesized substance, or a part of these substances. Specific examples of the extracellular matrix include fibronectin, gelatin, collagen, collagen peptides, laminin, and polylysine. Examples of the extracellular matrix are not limited to these and include those disclosed in Japanese Patent Application Publication No. 2007-228921 (Japanese Patent No. 4919464) and Japanese Patent Application Publication No. 2012-115254.

The cellular tissue may comprise one extracellular matrix or two or more extracellular matrices. In one embodiment, a combination of extracellular matrices comprised in the cellular tissue includes a combination of a first substance and a second substance that interacts with the first substance. Examples of the combination of the first substance and the second substance include a combination of a polymer having an RGD sequence and a polymer that interacts with the polymer having an RGD sequence and a combination of a positively charged polymer and a negatively charged polymer. Specific examples of the combination of the first substance and the second substance include a combination of fibronectin and gelatin (or a collagen peptide), a combination of fibronectin and s-polylysine, a combination of fibronectin and hyaluronic acid, a combination of fibronectin and dextran sulfate, a combination of fibronectin and heparin, and a combination of laminin and gelatin.

<Mesothelial Cell Layer>

The mesothelial cell layer is formed to cover the surface of the cellular tissue. In one embodiment, the mesothelial cell layer is placed on an upper surface of the cellular tissue. In other embodiment, the mesothelial cell is a cell that forms an outermost layer (mesothelium). In another embodiment, the mesothelial cell layer is substantially a mesothelial cell monolayer.

In one embodiment, the density of mesothelial cell in the mesothelial cell layer ranges from $5.2 \times 10^2$ cells/mm$^2$ to $2.5 \times 10^3$ cells/mm$^2$. In other embodiment, the density of mesothelial cell in the mesothelial cell layer is preferably from $5.2 \times 10^2$ cells/mm$^2$ to $1.3 \times 10^3$ cells/mm$^2$ in terms of optimum conditions for forming a mesothelial cell monolayer.

In one embodiment, adjacent mesothelial cells preferably form cell-cell adhesion. In other embodiment, the mesothelial cell layer has one microvillus or a plurality of microvilli on the surface thereof. This configuration can reproduce a peritoneal tissue structure, preferably a peritoneal tissue function, more similar to those in a living organism.

In one embodiment, the mesothelial cell may be derived from either a human or a non-human animal. In other embodiment, the mesothelial cell may be a cell derived from a mesenchymal stem cell, from an embryonic stem cell, from an induced pluripotent stem cell, or the like. In another embodiment, the mesothelial cell may be a cultured cell. Examples of the cultured cell include, but are not limited to, a primary cultured cell, a passaged cell, and a cell derived from a cell line.

In one embodiment, the artificial peritoneal tissue of the present disclosure can be used in drug evaluation, for example, for testing drug efficacy, pharmacological properties and safety of a test substance to the peritoneum. In other embodiment, the artificial peritoneal tissue of the present disclosure can be used in screening for a candidate substance for an active ingredient.

In another embodiment, the artificial peritoneal tissue of the present disclosure can be used in basic research and evaluation of the peritoneum in a living organism. In yet another embodiment, the artificial peritoneal tissue of the present disclosure can be used as a lab tool for use in research and evaluation of a peritoneum's inherent function, such as absorption and transportation of body fluid, immune cells, and the like.

In another embodiment, the artificial peritoneal tissue of the present disclosure can be used in evaluation of the behavior of a cancer cell in the peritoneal tissue. In yet another embodiment, the artificial peritoneal tissue of the present disclosure can be used in screening for a candidate substance for an active ingredient of a medicament to be used in treating the peritoneum, such as anti-cancer agents. In yet another embodiment, the artificial peritoneal tissue of the present disclosure can be used as a lab tool for use in reproducing cancer invasion and cancer metastasis caused by peritoneal metastasis or as a lab tool for use in investigating the mechanisms thereof.

In another embodiment, the artificial peritoneal tissue of the present disclosure can be used as a lab tool for use in investigating the mechanism through which peritoneal dialysis causes peritoneal hypofunction, peritoneal hardening or thickening, or encapsulating peritoneal sclerosis (EPS).

In another embodiment, the artificial peritoneum of the present disclosure can be used as a graft for transplantation.

[Method for Producing Artificial Peritoneal Tissue]

In other aspect, the present disclosure relates to a method for producing an artificial peritoneal tissue comprising a cellular tissue and a mesothelial cell layer that covers a surface of the cellular tissue, the cellular tissue comprising a fibroblast, an extracellular matrix, and at least one of a vascular endothelial cell and a lymphatic endothelial cell forming a lumen (hereinafter, also called "the method for producing an artificial peritoneal tissue of the present disclosure"). The method for producing an artificial peritoneal tissue of the present disclosure comprises culturing at least one of a vascular endothelial cell and a lymphatic endothelial cell, a fibroblast, and an extracellular matrix to form the cellular tissue, and placing a mesothelial cell on the cellular tissue.

In one embodiment, the method for producing an artificial peritoneal tissue of the present disclosure can produce an artificial peritoneal tissue in which adjacent vascular endothelial cells form cell-cell adhesion and a lumen having a vesicle-like structure formed on an inner wall thereof (blood-vessel-like structure) is comprised. In other embodiment, the method for producing an artificial peritoneal tissue of the present disclosure can produce an artificial peritoneal tissue that comprises a lumen having an area where adjacent lymphatic endothelial cells form cell-cell adhesion and an area where adjacent lymphatic endothelial cells are away from each other (lymphatic-vessel-like structure). Therefore, in one embodiment, the method for producing an artificial peritoneal tissue of the present disclosure can produce an artificial peritoneal tissue that can reproduce an environment more similar to the environment of peritoneal tissue in a human living body. In other embodiment, the method for producing an artificial peritoneal tissue of the present disclosure can produce an artificial peritoneal tissue that is excellent in tissue reproducibility. In one embodiment, the method for producing an artificial peritoneal tissue of the present disclosure can produce the artificial peritoneal tissue of the present disclosure.

<Formation of Cellular Tissue>

Forming the cellular tissue comprises culturing at least one of a vascular endothelial cell and a lymphatic endothelial cell, a fibroblast, and an extracellular matrix. In one embodiment, forming the cellular tissue can be performed by sandwiching a single layer including a vascular endothelial cell and/or a lymphatic endothelial cell between fibroblast layers and conducting culturing with this configuration (a sandwich method). In other embodiment, forming the cellular tissue can be performed by placing a mixture of a fibroblast and at least one of a vascular endothelial cell and a lymphatic endothelial cell on a base and conducting culturing (a mixture method). In another embodiment, forming the cellular tissue may be performed by a combination of the sandwich method and the mixture method.

In one embodiment, culturing at least one of a vascular endothelial cell and a lymphatic endothelial cell, a fibroblast, and an extracellular matrix can be performed by coating these cells with a coating film that contains an extracellular matrix, arranging the resulting cells in a three-dimensional manner, and conducting culturing. Alternatively, the culturing may be performed by Layer-by-Layer assembling (LbL) (a monolayer of) these cells and an extracellular matrix and conducting culturing. In one embodiment, forming the cellular tissue may be performed by using a combination of a cell coated with a coating film that contains an extracellular matrix and a non-coated cell. In one embodiment, forming the cellular tissue using the coated cell can be performed based on such a method as described in the Examples or as disclosed in Japanese Patent Application Publication No. 2012-115254. In other embodiment, forming the cellular tissue by the LbL technique can be performed based on such a method as disclosed in Japanese Patent Application Publication No. 2007-228921 (Japanese Patent No. 4919464).

In one embodiment, the number of fibroblast layers to be placed is preferably 4 or more, more preferably 5, 6, 7, 8, 9, 10, or more.

In one embodiment, the placing (seeding) density of the fibroblast is preferably from $4 \times 10^8$ cells/cm$^3$ to $1.2 \times 10^9$ cells/cm$^3$, more preferably from 1×10$^9$ cells/cm$^3$ to 1.2×10$^9$ cells/cm$^3$, for the reasons of creating an optimum microenvironment for lumen formation and mesothelial cell monolayer formation.

<Formation of Mesothelial Cell Layer>

In one embodiment, forming the mesothelial cell layer comprises placing a mesothelial cell on the cellular tissue and conducting culturing. In other embodiment, the mesothelial cell is placed to cover the surface of the cellular tissue. In another embodiment, the mesothelial cell is placed so that substantially a mesothelial cell monolayer is to be formed.

In one embodiment, the placing (seeding) density of the mesothelial cell ranges from 5.2×10$^2$ cells/mm$^2$ to 2.5×10$^3$ cells/mm$^2$. In other embodiment, the density is preferably from 5.2×10$^2$ cells/mm$^2$ to 1.3×10$^3$ cells/mm$^2$ in terms of optimum conditions for forming a uniform mesothelial cell monolayer.

In one embodiment, in terms of forming a uniform mesothelial cell monolayer, the mesothelial cell is preferably seeded without coating its surface with an extracellular matrix. In other embodiment, in terms of forming a structure where the mesothelial cell is merged with the cellular tissue via an extracellular matrix and thereby obtaining an artificial peritoneal tissue more similar to the peritoneum tissue of a living organism, it is preferable that the mesothelial cell is seeded on the cellular tissue 6 to 24 hours after a cell for forming the cellular tissue (for example, a fibroblast to form an uppermost layer of the cellular tissue) is seeded. In one embodiment, in terms of forming adhesion between adjacent mesothelial cells and thereby obtaining an artificial peritoneal tissue more similar to the peritoneum tissue of a living organism, the culturing is preferably continued for 5 days or longer after the mesothelial cell is seeded.

[Method of Evaluating Behavior of Cancer Cell in Artificial Peritoneal Tissue]

In another aspect, the present disclosure relates to a method for evaluating behavior of a cancer cell in an artificial peritoneal tissue, the method comprising: co-culturing the artificial peritoneal tissue of the present disclosure and a cancer cell and monitoring the behavior of the cancer cell in the artificial peritoneal tissue thus co-cultured (hereinafter, also called "the evaluation method of the present disclosure").

Examples of the evaluation of the behavior of a cancer cell include, but are not limited to, evaluation or monitoring of the abilities of the cancer cell to proliferate, invade, and metastasize within the artificial peritoneal tissue, and an effect on other cells, as well as evaluation or monitoring of suppression of these abilities and/or the effect. The evaluation method in the present disclosure can also comprise observing, for example, the presence or absence of a variation of the reproduction caused with a change in culturing conditions and/or external conditions in reproduction of growth, invasion, and/or metastasis of cancer by the use of the artificial peritoneal tissue of the present disclosure.

In one embodiment, co-culturing the artificial peritoneal tissue and a cancer cell can be performed by placing a cancer cell on the artificial peritoneal tissue and conducting culturing. As a medium, a medium described above can be used. A culturing temperature is as described above.

In one embodiment, the evaluation method of the present disclosure may comprise contacting a test substance with the artificial peritoneal tissue co-cultured with a cancer cell.

In one embodiment, the artificial peritoneal tissue of the present disclosure can reproduce growth, invasion, and/or metastasis of cancer when co-cultured with a cancer cell.

Therefore, in one embodiment, the present disclosure relates to a model of cancer invasion in a peritoneal tissue that contains the artificial peritoneal tissue of the present disclosure and a cancer cell.

[Screening Method]

In another aspect, the present disclosure relates to a method for screening for a candidate substance for an active ingredient of an anti-cancer agent, the method comprising: co-culturing the artificial peritoneal tissue of the present disclosure and a cancer cell; contacting a test substance with the artificial peritoneal tissue that has been contacted with the cancer cell; and evaluating the action of the test substance to the artificial peritoneal tissue that has been contacted with the cancer cell (hereinafter, also called "the screening method of the present disclosure"). In one embodiment, the screening method of the present disclosure using the artificial peritoneal tissue of the present disclosure can allow a test substance to be evaluated under an environment more similar to an environment in a living organism, as compared to a conventional method.

Examples of the action of a test substance include inhibition of at least one selected from the group consisting of metastasis, invasion, and growth of a cancer cell.

[Screening Kit]

In another aspect, the present disclosure relates to a kit that is used in screening for a candidate substance for an active ingredient of an anti-cancer agent, the kit comprising the artificial peritoneal tissue of the present disclosure and a cancer cell (hereinafter, also called "the screening kit of the present disclosure"). In one embodiment, the screening kit of the present disclosure can be used to implement the screening method of the present disclosure.

In one embodiment, the screening kit of the present disclosure may further comprise a product that contains at least one of a reagent, a material, a tool, and a device each for use in a certain examination, and written instructions (a written manual).

Hereinafter, the present disclosure will be described in detail referring to preferable embodiments. The present disclosure, however, is not limited to the following embodiments.

First, a fibroblast having a coating film (hereinafter, also called "coated fibroblast") is prepared. In one embodiment, the coated fibroblast can be formed by Layer-by-Layer assembling fibronectin and gelatin.

Then, the coated fibroblasts are seeded on a base such as a cell-culture insert, followed by culturing. Seeding the coated fibroblasts is performed in such a way that the number of layers of the coated fibroblasts is 4 or more, preferably 5, 6, 7, 8, 9, 10, or more. In one embodiment, the density of the fibroblasts thus seeded ranges from 1×10$^2$ cells/cm$^3$ to 1×10$^9$ cells/cm$^3$, from 1×10$^4$ cells/cm$^3$ to 1×10$^8$ cells/cm$^3$, or from 1×10$^5$ cells/cm$^3$ to 1×10$^7$ cells/cm$^3$.

In one embodiment, the culturing is performed with a media added thereto. Examples of the medium include, but are not limited to, Eagle's MEM Medium, Dulbecco's Modified Eagle Medium (DMEM), Modified Eagle Medium (MEM), Minimum Essential Medium, RDMI, and GlutaMax Medium. Those skilled in the art can select a medium appropriately depending on the type of the cell to be cultured. In one embodiment, the medium is supplemented with serum. The culturing temperature is, for example, 37° C. The culturing duration ranges from, for example, 6 hours to 24 hours. Those skilled in the art can set the culturing temperature and the culturing duration appropriately depending on the type of the cell to be cultured.

Then, vascular endothelial cells are seeded on the resulting fibroblast laminate, followed by culturing. The vascular endothelial cells are placed so that a vascular endothelial cell monolayer is to be formed. The vascular endothelial cell may or may not be coated with an extracellular matrix. The culturing conditions are as described above.

Then, coated fibroblasts are seeded on the vascular endothelial cells, followed by culturing. Seeding and culturing the coated fibroblasts are performed in the same manner as above.

Then, mesothelial cells are seeded on the resulting cellular tissue, followed by culturing. In terms of efficiently forming a mesothelial cell monolayer, the mesothelial cells are not coated with an extracellular matrix. The seeding density of the mesothelial cells is as described above. The medium and the culturing temperature are as described above for the cellular tissue. The culturing duration varies depending on the culturing temperature, but is, for example, 5 days or longer. In one embodiment, the culturing duration preferably ranges from 5 days to 14 days. Thus, an artificial peritoneal tissue comprising a cellular tissue with an internal capillary vessel-like structure and a mesothelial cell layer can be formed.

This embodiment adopts, as an example, a configuration in which a vascular endothelial layer (monolayer) is sandwiched between fibroblast layers (4 or more fibroblast layers), but the present disclosure is not limited to this configuration. The cellular tissue may be formed by seeding a mixture of a vascular endothelial cell and the coated fibroblast and performing culturing.

This embodiment adopts, as an example, use of a fibroblast and a vascular endothelial cell for producing a cellular tissue, but the present disclosure is not limited to this configuration. In one embodiment, a cellular tissue may be produced by using a pericyte, a smooth muscle cell, and a mesenchymal stem cell instead of or in combination with a fibroblast. In other embodiment, a cellular tissue may be produced by using a lymphatic endothelial cell instead of or in combination with a vascular endothelial cell.

The present disclosure may relate to the following embodiments.

[1] An artificial peritoneal tissue comprising:
a cellular tissue; and
a mesothelial cell layer that covers a surface of the cellular tissue,
the cellular tissue comprising a fibroblast, an extracellular matrix, and at least one of a vascular endothelial cell and a lymphatic endothelial cell forming a lumen.

[2] The artificial peritoneal tissue according to [1], wherein the lumen has at least one of a capillary vessel-like structure and a lymphatic-vessel-like structure.

[3] The artificial peritoneal tissue according to [1], wherein
the mesothelial cell layer forms a tectorial structure, and
a mesothelial cell in the mesothelial cell layer is bound via the extracellular matrix to a tissue constituted of the fibroblast and at least one of the capillary vessel-like structure and the lymphatic-vessel-like structure,

[4] The artificial peritoneal tissue according to any one of [1] to [3], wherein the mesothelial cell layer has a microvillus on a surface thereof.

[5] The artificial peritoneal tissue according to any one of [1] to [4], wherein the extracellular matrix comprises at least fibronectin and gelatin.

[6] The artificial peritoneal tissue according to any one of [1] to [4], wherein the extracellular matrix contains a first substance and a second substance and a combination of the first substance and the second substance is selected from the group consisting of the followings:
(a) fibronectin and gelatin;
(b) fibronectin and s-polylysine;
(c) fibronectin and hyaluronic acid;
(d) fibronectin and dextran sulfate;
(e) fibronectin and heparin; and
(f) laminin and gelatin.

[7] The artificial peritoneal tissue according to [6], wherein the combination of the first substance and the second substance is a combination of fibronectin and gelatin.

[8] A method for producing an artificial peritoneal tissue comprising a cellular tissue and a mesothelial cell layer that covers a surface of the cellular tissue, the cellular tissue comprising a fibroblast, an extracellular matrix, and at least one of a vascular endothelial cell and a lymphatic endothelial cell forming of a lumen, the method comprising:
culturing at least one of a vascular endothelial cell and a lymphatic endothelial cell, a fibroblast, and an extracellular matrix to form the cellular tissue; and
placing a mesothelial cell on the cellular tissue.

[9] The method for producing an artificial peritoneal tissue according to [8], wherein forming the cellular tissue comprises placing a fibroblast coated with the extracellular matrix.

[10] The method for producing an artificial peritoneal tissue according to [8] or [9], wherein the mesothelial cell is placed at a density ranging from $5.2 \times 10^2$ cells/mm$^2$ to $1.3 \times 10^3$ cells/mm$^2$.

[11] The method for producing an artificial peritoneal tissue according to any one of [8] to [10], wherein the extracellular matrix comprises at least fibronectin and gelatin.

[12] The method for producing an artificial peritoneal tissue according to any one of [8] to [10], wherein the extracellular matrix contains a first substance and a second substance and a combination of the first substance and the second substance is selected from the group consisting of the followings:
(a) fibronectin and gelatin;
(b) fibronectin and s-polylysine;
(c) fibronectin and hyaluronic acid;
(d) fibronectin and dextran sulfate;
(e) fibronectin and heparin; and
(f) laminin and gelatin.

[13] The method for producing an artificial peritoneal tissue according to [12], wherein the combination of the first substance and the second substance is a combination of fibronectin and gelatin.

[14] The method for producing an artificial peritoneal tissue according to any one of [8] to [13], which produces the artificial peritoneal tissue according to any one of [1] to [7].

The present disclosure will be further described by way of examples. The present disclosure, however, should not be construed by being limited to these examples.

In the present specification, the following abbreviations are used.

50-mM Tris-HCl (pH 7.4): 50-mM Tris adjusted to pH 7.4 with HCl (manufactured by Nacalai Tesque) and then subjected to wet heat sterilization in an autoclave (121° C., 20 minutes)

BFN: Fibronectin from bovine plasma (manufactured by Sigma-Aldrich)

FN liquid: 0.04 mg of BFN/1 ml of 50-mM Tris-HCl (pH 7.4)
G liquid: 0.04 mg of Gelatin/1 ml of 50-mM Tris-HCl (pH 7.4)

EXAMPLES

[Preparation of Coated Cell]

Coated cella were prepared based on description in Japanese Patent Application Publication No. 2012-115254.
<Normal Human Dermal Fibroblast (NHDF)>

NHDFs were used as cells, and fibronectin (FN) and gelatin (G) were used as extracellular matrix components. The cells were immersed alternately in an FN liquid and in a G liquid, 9 times in total. Thus, coated NHDFs having an $(FN/G)_4FN$ film formed on the surface thereof were prepared (coating film thickness: about 10 nm). Immersion in the FN liquid was performed 5 times, and immersion in the G liquid was performed 4 times. The thickness of the coating film was measured by a method described in the Example of Japanese Patent Application Publication No. 2012-115254.
<Human Umbilical Vein Endothelial Cell (HUVEC)>

Coated HUVECs having an $(FN/G)_4FN$ film formed thereon were prepared in the same manner as above except that HUVECs were used instead of NHDFs (coating film thickness: about 10 nm).
<Human Dermal Lymphatic Endothelial Cell (HDLEC)>

Coated HDLECs having an $(FN/G)_4FN$ film formed thereon were prepared in the same manner as above except that HDLECs were used instead of NHDFs (coating film thickness: about 10 nm).

Example 1

[Preparation of Artificial Peritoneal Tissue Having Vascular Network Structure]

An insert having a porous polyester membrane (pore size: 0.4 μm) and a 24-well multiwell plate were obtained for use as a culturing container. A bottom surface of the insert was coated with BFN and then seeded with coated NHDFs ($4\times10^5$ cells/well), followed by culturing for 6 hours. Thus, NHDF layers (4 layers) were formed. On the resulting NHDF layers, coated HUVECs ($1\times10^5$ cells/well) were seeded, followed by culturing for 6 hours (an HUVEC monolayer was formed). On the resulting HUVEC layer, coated NHDFs were seeded ($4\times10^5$ cells/well), followed by culturing for 6 hours. Thus, NHDF layers (4 layers) were formed on the HUVEC layer. On the NHDF layers formed on the HUVEC layer, mesothelial cells derived from human greater omentum were seeded ($5\times10^4$ cells/well) ($1.3\times10^3$ cells/mm$^2$), followed by culturing for 5 days to obtain an artificial peritoneal tissue. The resulting artificial peritoneal tissue is shown in FIG. 1. As a medium, DMEM supplemented with 10% FBS was used. Culturing was performed at 5% $CO_2$ and 37° C. The resulting artificial peritoneal tissue had a thickness of 45 μm. The cellular tissue had a thickness of 42 μm. The capillary vessel-like structure had a diameter of 18 μm. The mesothelial cell layer had a thickness of 3 μm. These thickness measurements were obtained from immunostaining images.

FIG. 1A is an optical microscope image, and each of FIGS. 1B to 1F is a transmission electron microscope image. In FIGS. 1A to 1F, BV indicates a capillary vessel-like structure, MC indicates a mesothelial cell, Fb indicates a fibroblast, and ECM indicates an extracellular matrix. The arrows in FIG. 1A show a sheet structure of mesothelial cells. As shown in FIGS. 1A to 1F, it was observed that the resulting artificial peritoneal tissue included a lumen constituted of vascular endothelial cells as well as a connective tissue layer containing fibroblasts and an extracellular matrix, and the surface of the connective tissue layer was covered with a mesothelial cell monolayer and was a similar configuration to that of the peritoneum in a living organism. As shown by the arrow in FIG. 1C, adhesion between adjacent mesothelial cells was observed. As shown in FIG. 1D, microvilli were observed on the surface of the mesothelial cell layer. As shown in FIG. 1E, vascular endothelial cells forming the lumen were overlaid one another and adhered to each other, suggesting the presence of cell-cell adhesion in these areas (shown by the arrows in the figure). FIG. 1F is an expanded partial view of vascular endothelial cells forming a lumen. As shown in FIG. 1F, it was observed that an inner wall of the lumen was rich in vesicle-like structure (shown by the arrowheads in the figure), which are abundantly distributed on a capillary wall in a living organism.

Example 2

[Preparation of Artificial Peritoneal Tissue Having Lymphatic Network Structure]

An artificial peritoneal tissue was prepared in the same manner as in Example 1 except that coated HDLECs were used instead of coated HUVECs. The resulting artificial peritoneal tissue is shown in FIG. 2. The resulting artificial peritoneal tissue had a thickness of 44 μm. The cellular tissue had a thickness of 41 μm. The lymphatic-vessel-like structure had a diameter of 13 μm. The mesothelial cell layer had a thickness of 3 μm. FIG. 2A is an optical microscope image, and each of FIG. 2B to 2D is a transmission electron microscope image. In FIGS. 2A to 2D, L indicates a lymphatic-vessel-like structure, Fb indicates a fibroblast, and ECM indicates an extracellular matrix. The arrows in FIG. 2A show a sheet structure of mesothelial cells. The resulting artificial peritoneal tissue comprises a lumen constituted of lymphatic endothelial cells as well as a connective tissue layer containing fibroblasts and an extracellular matrix. As shown in FIG. 2A, it was observed that the surface of the connective tissue layer was covered with a mesothelial cell monolayer. As shown in FIGS. 2B to 2D, it was confirmed that the lumen constituted of lymphatic endothelial cells had an area where lymphatic endothelial cells were adhered to each other (shown by the arrow in FIG. 2B) and an area where lymphatic endothelial cells were separated from each other (shown by the arrow in FIG. 2D), and it had a configuration similar to a lymphatic capillary in a living organism.

By the same method but with the use of a mesothelial cell line adaptable to long-term passaging instead of a mesothelial cell derived from human greater omentum, an artificial peritoneal tissue having a vascular network structure as well as an artificial peritoneal tissue having a lymphatic network structure were prepared.

The invention claimed is:

1. A method for producing an artificial peritoneal tissue comprising a cellular tissue and a mesothelial cell layer that covers a surface of the cellular tissue, wherein the cellular tissue consists of a fibroblast, an extracellular matrix, and at least one of a vascular endothelial cell and a lymphatic endothelial cell forming at least one selected from the group consisting of a vascular network structure and a lymphatic network structure, the method comprising:

culturing at least one of a vascular endothelial cell and a lymphatic endothelial cell, a fibroblast, and an extracellular matrix, thereby forming the cellular tissue; and placing a mesothelial cell on the cellular tissue, wherein the forming the cellular tissue comprises:

placing a fibroblast coated with the extracellular matrix; and placing at least one of a vascular endothelial cell coated with the extracellular matrix and a lymphatic endothelial cell coated with the extracellular matrix, thereby forming the at least one selected from the group consisting of a vascular network structure and a lymphatic network structure, wherein adjacent mesothelial cells form cell-cell adhesion in the artificial peritoneal tissue, wherein the mesothelial cell layer has a microvillus on a surface thereof, wherein the extracellular matrix consists of fibronectin and gelatin, and wherein the coated fibroblast and at least one of the coated vascular endothelial cell and the coated lymphatic endothelial cell are stacked on each other.

2. The method according to claim 1, wherein the mesothelial cell is placed at a density ranging from $5.2 \times 10^2$ cells/mm$^2$ to $1.3 \times 10^3$ cells/mm$^2$.

3. The method according to claim 1, wherein the produced artificial peritoneal tissue comprises:

the cellular tissue; and the mesothelial cell layer that covers a surface of the cellular tissue, wherein the cellular tissue consists of fibroblast, fibronectin, gelatin, and at least one selected from the group consisting of the vascular network structure and the lymphatic network structure.

\* \* \* \* \*